United States Patent [19]

Weng et al.

[11] Patent Number: 5,782,766
[45] Date of Patent: Jul. 21, 1998

[54] METHOD AND APPARATUS FOR GENERATING AND DISPLAYING PANORAMIC ULTRASOUND IMAGES

[75] Inventors: Lee Weng; Arun P. Tirumalai; Levin Nock, all of Issaquah, Wash.

[73] Assignee: Siemens Medical Systems, Inc., Iselin, N.J.

[21] Appl. No.: 747,429

[22] Filed: Nov. 19, 1996

Related U.S. Application Data

[63] Continuation-in-part of Ser. No. 414,978, Mar. 31, 1995, Pat. No. 5,575,286, and Ser. No. 622,904, Mar. 29, 1996, Pat. No. 5,655,535.

[51] Int. Cl.$^6$ .................................................. A61B 8/00
[52] U.S. Cl. ............................................. 600/443; 128/916
[58] Field of Search .......................... 128/653.1, 653.2, 128/654, 659, 660.01, 660.07, 660.08, 660.1, 662.06; 600/437, 443, 444, 1–30, 98

[56] References Cited

U.S. PATENT DOCUMENTS

| | | | |
|---|---|---|---|
| 5,181,513 | 1/1993 | Touboul et al. | 128/660.07 |
| 5,184,622 | 2/1993 | Tomura | 128/660.07 |
| 5,211,167 | 5/1993 | Ameuori | 128/662.06 X |
| 5,494,040 | 2/1996 | Nakao et al. | 128/662.06 |
| 5,575,286 | 11/1996 | Weng et al. | 128/653.1 |

*Primary Examiner*—Francis Jaworski

[57] ABSTRACT

An image registration based method and a corresponding apparatus are provided for creating composite, panoramic images, in which consecutive ultrasonic image frames are correlated in order to derive transducer motion information. The individual images can be divided into several smaller sub-image regions and a fast and robust image motion detection algorithm is used to measure the sub-image motion and then to determine an initial estimation of the local motion vectors. The initial estimation is combined with two measurement parameters by use of a fuzzy logic technique to derive a final estimation of the local motion vectors. The final local motion vectors are then used to estimate global image motion. Compound images are then diplayed based on the derived global image motion. The speed of motion of the transducer is also estimated and a "speedometer" is displayed to help the user move the transducer within efficient speed ranges. Image frames may also be selectively "zoomed" in on and displayed in an undistorted manner. Distance scales are generated for both the normally curved panoramic image and also the undistorted frame images. A frame guide is also displayed to help the user guide the transducer to area of greatest interest. Color-coded velocity or power information may also be superimposed on the panoramic image, and spectral Doppler data may also be displayed at selected points in the panoramic image. A memory map is preferably also displayed to indicate to the user how much image memory is remaining during a scan.

13 Claims, 12 Drawing Sheets

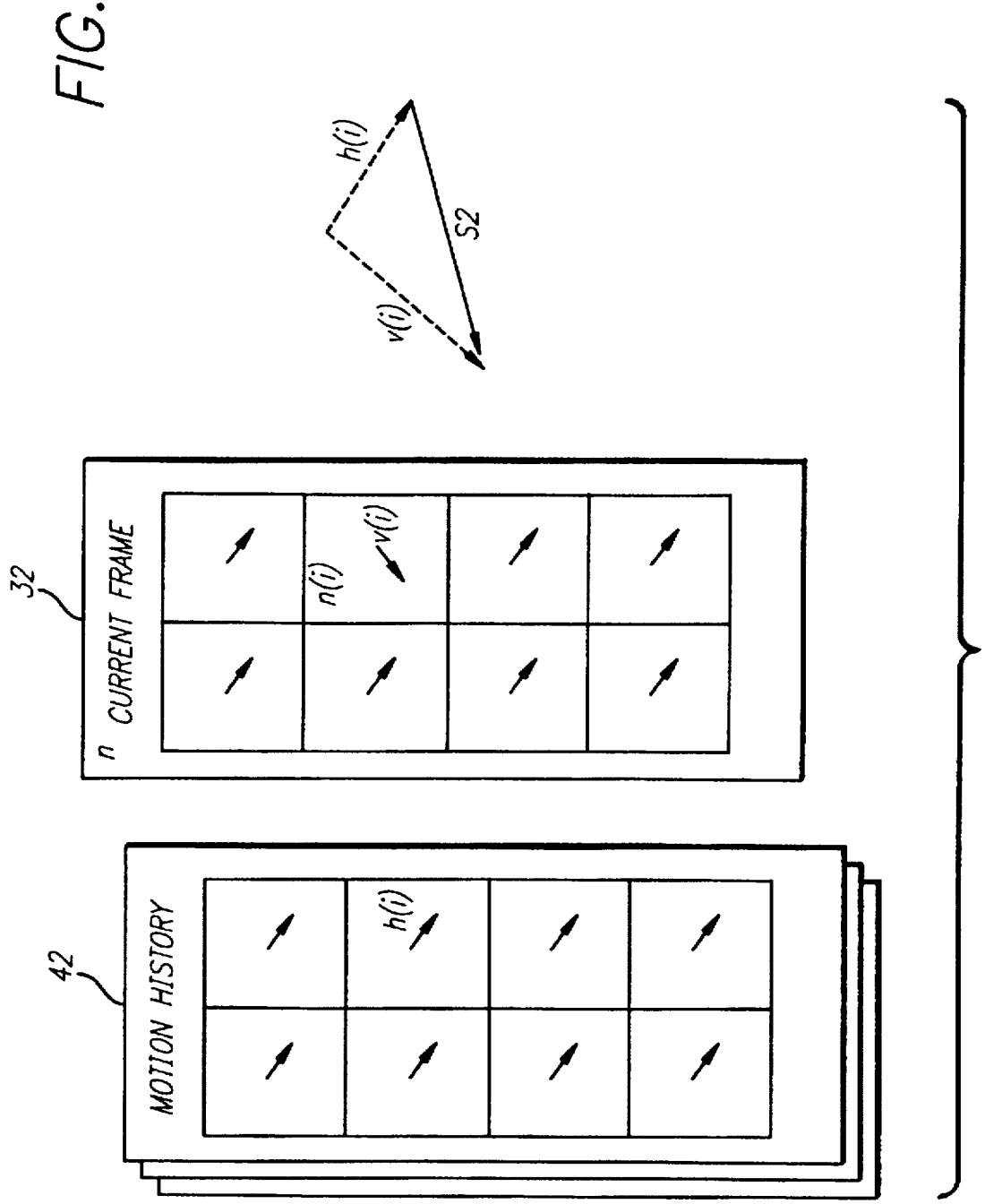

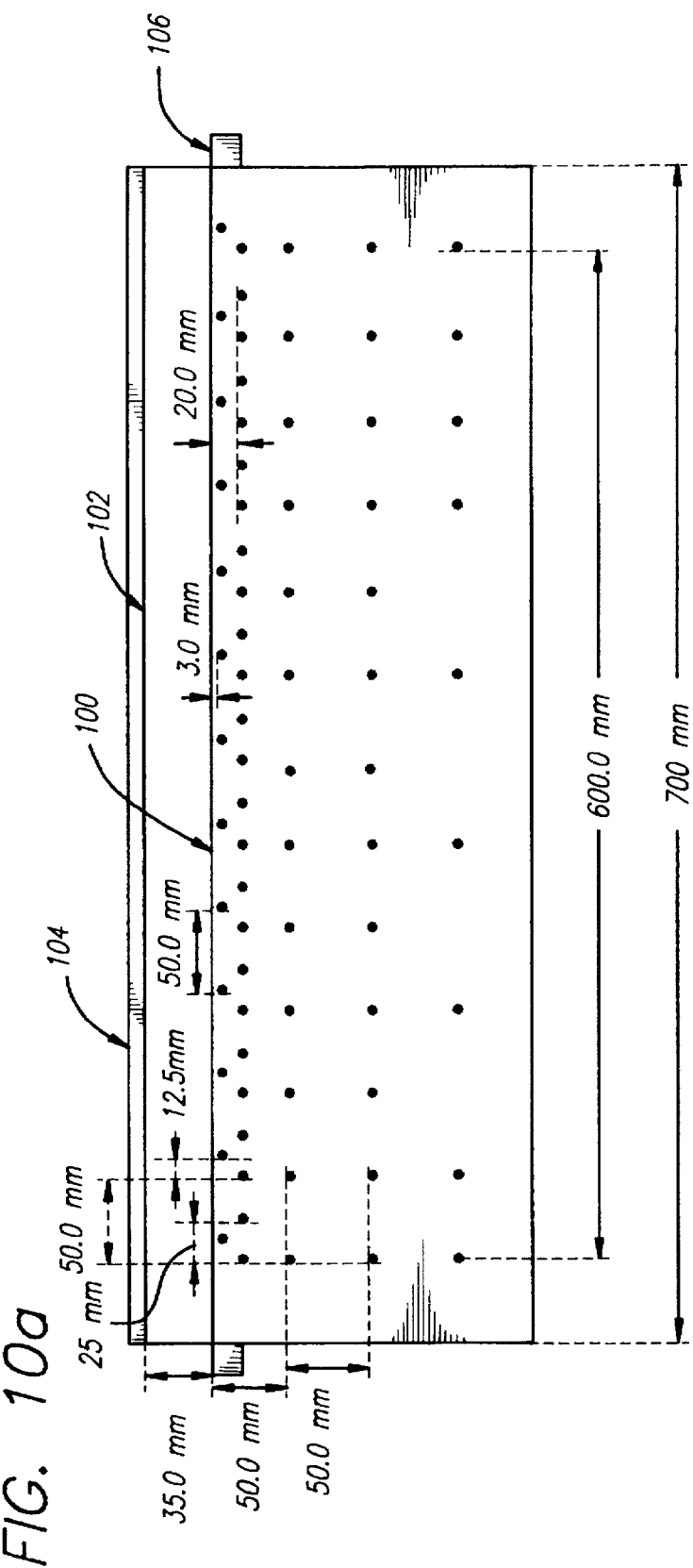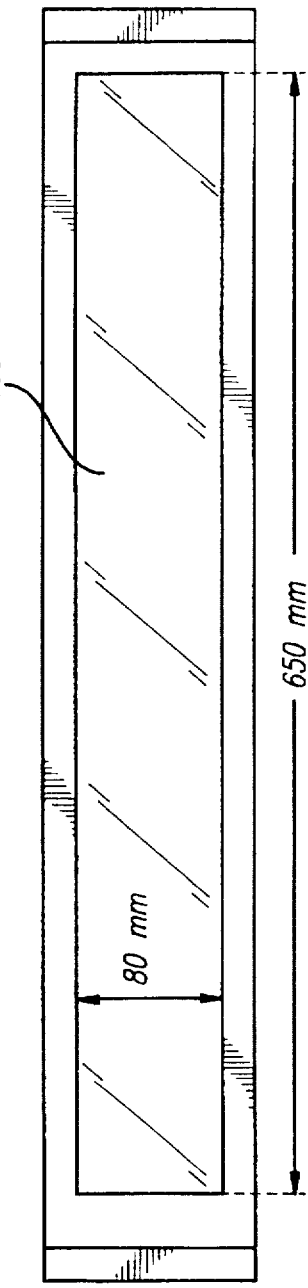
FIG. 10a
FIG. 10b

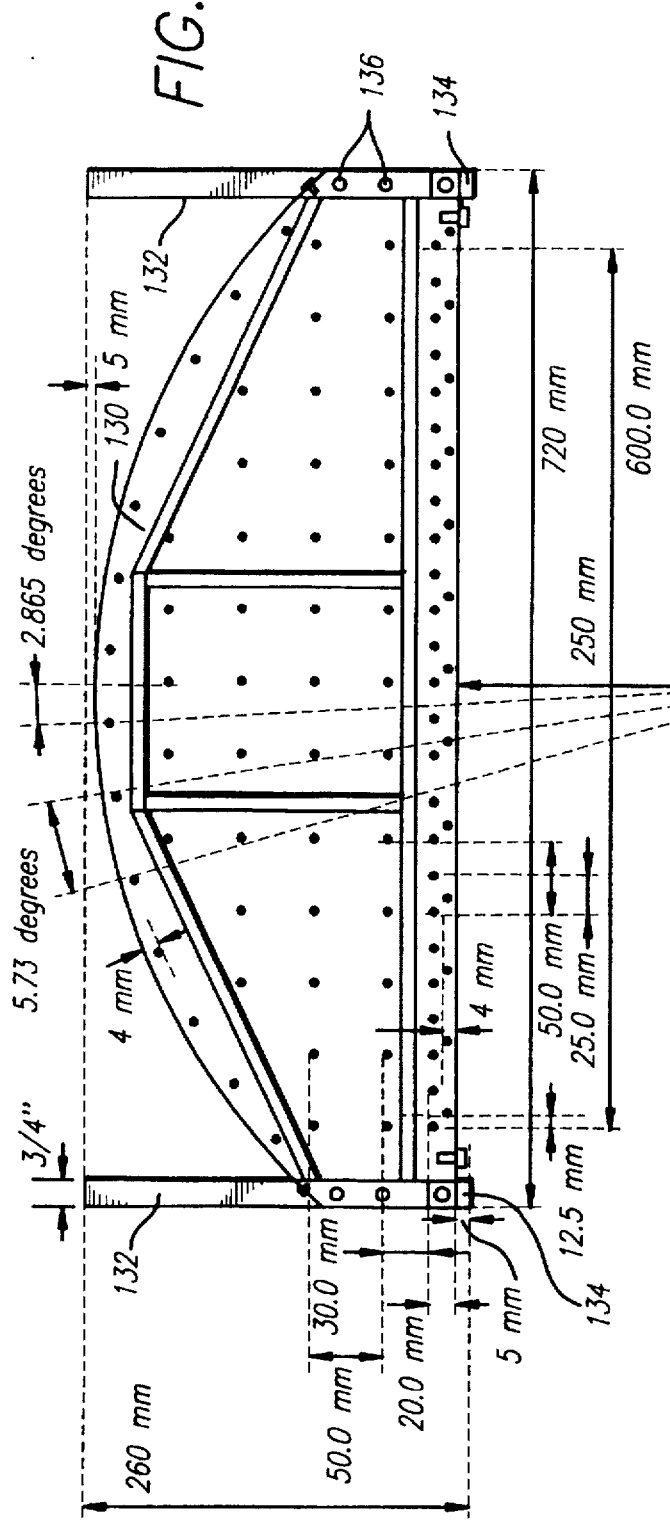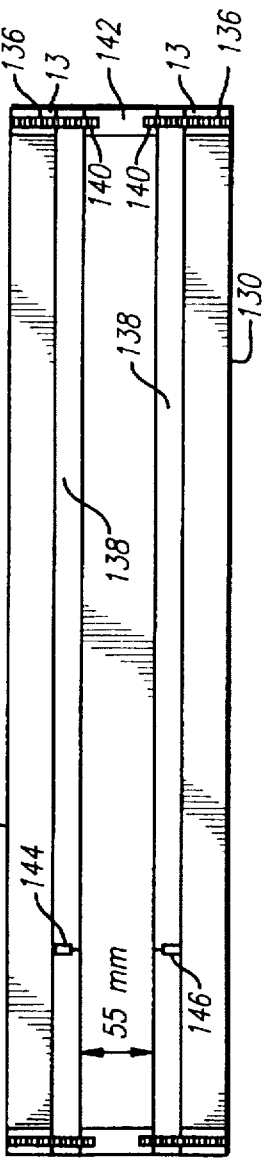
FIG. 11a
FIG. 11b

METHOD AND APPARATUS FOR GENERATING AND DISPLAYING PANORAMIC ULTRASOUND IMAGES

CROSS-REFERENCE TO RELATED APPLICATIONS

This application is a continuation-in-part of U.S. patent Application No. 08/414,978, filed Mar. 31, 1995 and now U.S. Pat. No. 5,575,286, with the title "Method and Apparatus for Generating Large Compound Ultrasound Image", and also a continuation-in-part of U.S. patent application No. 08/622,904, filed 29 Mar. 1996 and now U.S. patent No. 5,655,535, with the title "Three-Dimensional Ultrasound Field of View".

BACKGROUND OF THE INVENTION

1. Field of the Invention

This invention relates to ultrasonic diagnostic imaging, and more particularly, to an ultrasonic imaging system that is capable of producing a panoramic image having an extended field of view by correlating movement between consecutive image frames.

2. Description of Related Art

Ultrasonic imaging techniques are commonly used to produce two-dimensional diagnostic images of internal features of an object, such as a human anatomy. A diagnostic ultrasonic imaging system for medical use forms images of internal tissues of a human body by electrically exciting an acoustic transducer element or an array of acoustic transducer elements to generate short ultrasonic pulses that travel into the body. The ultrasonic pulses produce echoes as they reflect off of body tissues that appear as discontinuities or impedance changes to the propagating ultrasonic pulses. These echoes return to the transducer, and are converted back into electrical signals that are amplified and decoded to produce a cross-sectional image of the tissues. These ultrasonic imaging systems are of significant importance to the medical field by providing physicians with real-time, high resolution images of the internal features of a human anatomy without resort to more invasive exploratory techniques, such as surgery.

The acoustic transducer which radiates the ultrasonic pulses typically comprises a piezoelectric element or matrix of piezoelectric elements. As known in the art, a piezoelectric element deforms upon application of an electrical signal to produce the ultrasonic pulses. In a similar manner, the received echoes cause the piezoelectric element to deform and generate the corresponding electrical signal. The acoustic transducer is often packaged within a hand-held device that allows the physician substantial freedom to easily manipulate the transducer over a desired area of interest. The transducer can then be electrically connected via a cable to a central control device that generates and processes the electrical signals. In turn, the control device transmits the image information to a real-time viewing device, such as a video display terminal. The image information may also be stored so that other physicians may view the diagnostic images at a later date.

The individual images produced by such ultrasonic imaging systems comprise discrete frames, with each such frame having a field of view limited by the relatively narrow region traversed by the ultrasonic pulses. As the transducer is manipulated along the body surface to obtain images of an adjacent region in the anatomy, each previous image is replaced on the viewing device by a new image defined by the limited field of view of the transducer. While a skilled physician can usually interpret the discrete frames in order to obtain a clear mental picture of the entire region traversed by the transducer, the discrete frames cannot be easily tiled together to produce a single, contiguous image. This can represent a significant drawback of conventional ultrasonic imaging systems, since it is not always possible for the physician to fully appreciate the overall condition of the body by consideration of the discrete frames alone. In some extreme cases, important information concerning the condition of the body tissues can be overlooked with serious potential consequences for the patient.

Previously, it has been demonstrated that a real-time compound ultrasonic image could be generated by use of so-called compound B-scanners. These B-scanners utilize a transducer mounted on an arm assembly that constrains the transducer to move along a single plane or axis. Either the arm assembly or the transducer element itself can be provided with sensing devices that track the precise position of the transducer. This positional information could then be utilized to register each of the discrete image frames together into a single composite image. An example of a compound B-scanner utilizing angular sensing devices on an arm assembly is disclosed in U.S. Pat. No. 4,431,007, to Amazeen et al., for REFERENCED REALTIME ULTRASONIC IMAGE DISPLAY. Despite this potential improvement in the art, conventional compound B-scanners are awkward and inflexible to operate due primarily to the relatively bulky mechanical arm assembly. Moreover, the sensing devices add significant complexity and cost to the ultrasonic imaging system.

Thus, a critical need exists for a method to combine each of the discrete frames produced by an ultrasonic imaging system into a single image. The method should be compatible with modern hand-held ultrasonic transducers without needlessly encumbering the hand-held transducers with position sensing devices that increase the cost, weight and complexity of such imaging systems.

In order to improve the quality of the image produced, and thus to get more useful information from it, the system should ideally also guide the user in maneuvering the ultrasound transducer. The system should preferably also present the user with displayed information, in addition to the image itself, that helps the user in image interpretation.

SUMMARY OF THE INVENTION

This application provides a method and apparatus for generating a large compound ultrasonic image, referred to herein as an extended field of view or "panoramic" image. The method and apparatus preferably use image registration techniques for composition of panoramic images in order to eliminate the need for position-sensing devices altogether. The use of such devices is, however, also proposed in conjunction with the purely image-based registration techniques either in order to help calibrate the system or in those cases where the available processing power is not sufficient to enable image registration in real time using the preferred registration procedures. In the preferred image registration method and apparatus, consecutive moving image frames are correlated in order to derive the transducer motion information for panoramic image generation.

In particular, the method and apparatus recognizes that ultrasonic images from real-time scanning operations are highly correlated from one frame to another. Based on this recognition, the individual images are divided into several smaller sub-image regions, and a fast and robust image motion detection routine is used to measure the sub-image motion. The preferred motion detection routine includes a fast adaptive coarse/fine minimum-sum-absolute-difference (MSAD) search strategy to compute an initial estimation of the local motion vectors; other routines are, however, proposed. The initial estimation is then combined with two measurement parameters by use of a fuzzy logic technique to derive a final estimation of the local motion vectors. The final local motion vectors are applied to a least-squares (L-S) process in order to estimate global image motion. Finally, a fast display technique generates compound panoramic images based on the derived global image motion.

In the preferred embodiment of the invention, a variable scale "ruler" is generated and displayed on a display screen along with the panoramic image in order to give the user distance information even for the often curved image. Since a curved composite panoramic image may distort the relative positions of features within any given image frame, the invention preferably also includes a secondary image that shows an undistorted frame, which the user selects from among those that go into making up the panoramic image. A distance scale is then preferably also generated along with the undistorted frame in order to give accurate depth information about that frame. The ability to select individual frames and display them separately also allows the user to "zoom in" on frames of particular interest.

If the user moves the transducer too fast, then the system may not be able to generate and correlate frames fast and accurately enough to create a reliable compound image. Moreover, if the user moves the transducer too slowly, then the system's memory may fill with frame data that is duplicative, or not needed in order to produce a composite image of acceptable reliability and scope. The invention thus includes a "speedometer," which indicates to the user whether he is moving the transducer within a preferred speed range.

Since the amount of memory available for storage of image frame data is limited, the invention preferably also tracks memory availability and displays this to the user as an icon or other display feature.

In order to guide the user in real time to move the transducer probe to areas of greatest interest, the invention preferably also generates a frame outline and composition marker that shows the user which frame is currently being processed and which part of the frame is being used for image composition.

As one further embodiment of the invention, color-coding representing conventional speed-related "power-mode" image information or velocity-related "Doppler-mode" image information is preferably computed and superimposed on the panoramic image to give a panoramic "color" map of movement information in the area covered by the image. When computing Doppler information about a region interrogated using ultrasound, the Doppler spectra are typically also computed. These spectra themselves contain valuable information about their respective image frames and may be displayed along with the panoramic image near the frames they represent.

The invention also includes the possibility of superimposing color-coded Doppler power or flow velocity images onto or in place of the panoramic intensity-related image.

BRIEF DESCRIPTION OF THE DRAWINGS

FIG. 6 is a block diagram illustrating derivation of a local vector deviation factor for the minimum-sum-absolute-difference search.

DETAILED DESCRIPTION

This invention satisfies the critical need for a method and apparatus to combine each of the discrete image frames produced by an ultrasonic imaging system into a single, composite panoramic image. In the image registration method and apparatus of this invention, consecutive image frames are correlated in order to derive the transducer motion information for composite, panoramic imaging. Significantly, in the preferred embodiment of the invention, the motion information is derived without encumbering the hand-held transducer with position sensing devices that would otherwise increase the cost, weight and complexity of such ultrasonic imaging systems. In the detailed description that follows, like element numerals are used to describe like elements illustrated in one or more of the figures.

Figure 1:
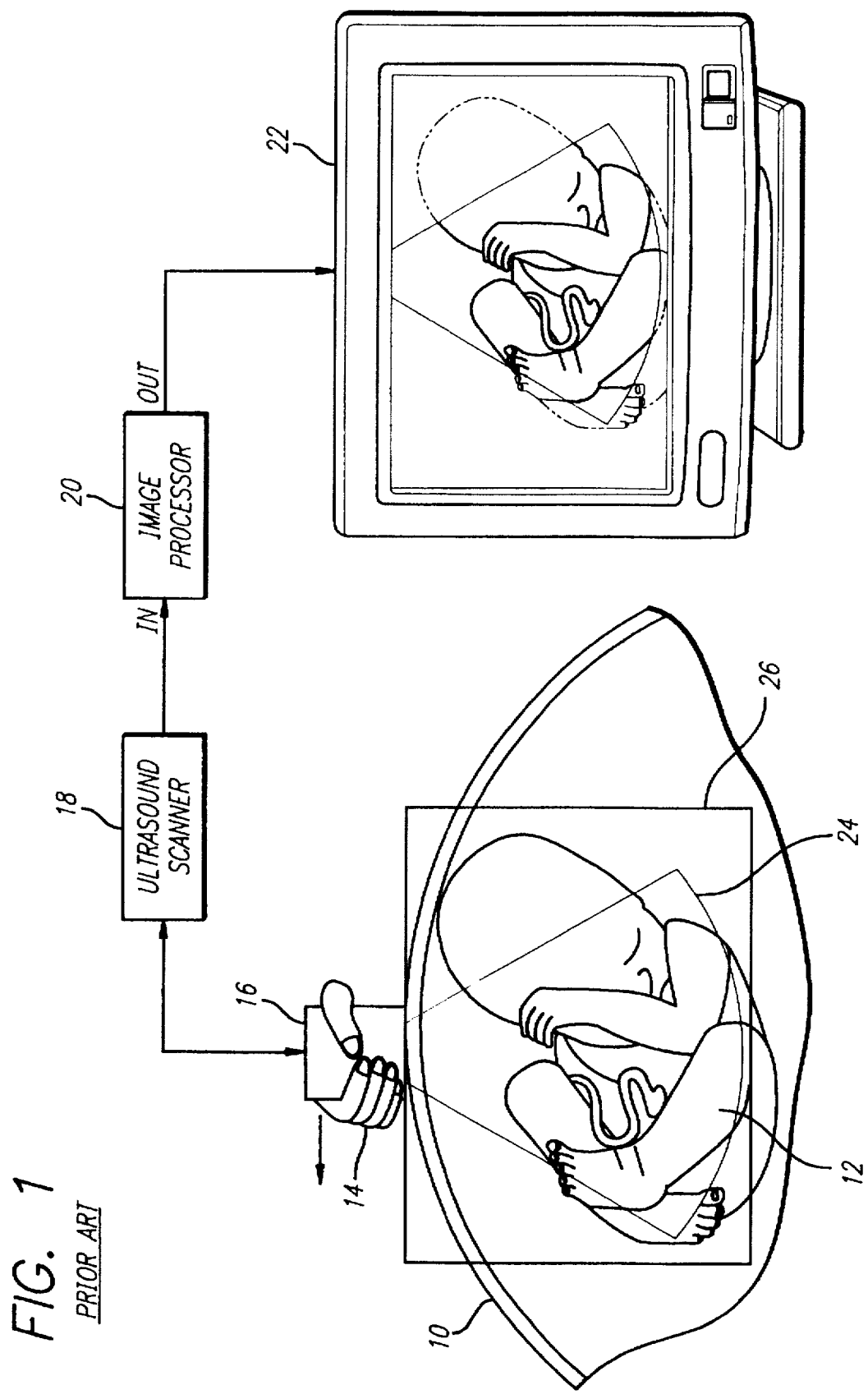
FIG. 1 is a partial perspective view of an ultrasonic imaging system adapted for real-time display of an exemplary fetal anatomy within a clinical environment.

In FIG. 1, a prior art ultrasonic imaging system adapted for real-time display within a clinical environment is illustrated. FIG. 1 illustrates the use of the invention for imaging a fetus 12. This is by way of example only. The system may be used to generate a panoramic image of any body structure and, indeed, as is explained further below, may also be combined with known techniques for generating flow information so as to create a panoramic image on which color flow data is superimposed.

In FIG. 1, a patient 10 carrying a fetus 12 is lying in a supine position to permit a physician or other technician 14 to perform an ultrasonic imaging operation. The imaging system comprises a scanhead 16 coupled to an ultrasound scanner 18. To perform the imaging operation, the physician 14 draws the scanhead 16 along the patient's skin surface in a direction which is parallel with the ultrasonic scan plane. An acoustically conductive, lubricating coupling agent may be applied to the skin prior to bringing the scanhead 16 into contact with the skin so as to improve acoustic coupling between the scanhead and the patient.

The scanhead 16 includes an ultrasonic transducer disposed at a surface thereof, comprising a piezoelectric element or matrix of individual piezoelectric elements. The ultrasound scanner 18 provides electrical signals to the scanhead 16 that cause it to generate ultrasonic pulses. The ultrasonic pulses 24 propagate in the scan plane through the skin of the patient 10 and echo off of the anatomical features of the fetus 12. The echoes return through the skin to the scanhead 16, which converts the echoes back into electrical signals received by the ultrasound scanner 18. The received electrical signals are then transmitted from the ultrasound scanner 18 to an image processor 20. The image processor 20 decodes the electrical signals into a two-dimensional, cross-sectional image that is displayed on the video display terminal 22. The image information may also be electronically stored in a memory medium, including a permanent storage medium such as a disk or tape drive, a temporary storage medium such as a solid state memory, or can be printed to a hard copy image such as a photograph.

The ultrasonic image displayed on the video display terminal 22 (or stored by use of the various other storage media described above) comprises only the information representative of the relatively narrow region traversed by the ultrasonic pulses 24. As illustrated in FIG. 1, only a portion of the anatomical features of the fetus 12 is displayed on the video display terminal 22. The region outside the sector of the ultrasonic pulses 24 (illustrated in phantom in FIG. 1) actually appears blank on the display device 22. As noted above, it would be very desirable to provide an image having an extended field of view (panoramic), such as a single image that includes the entire image region 26.

Figure 2:
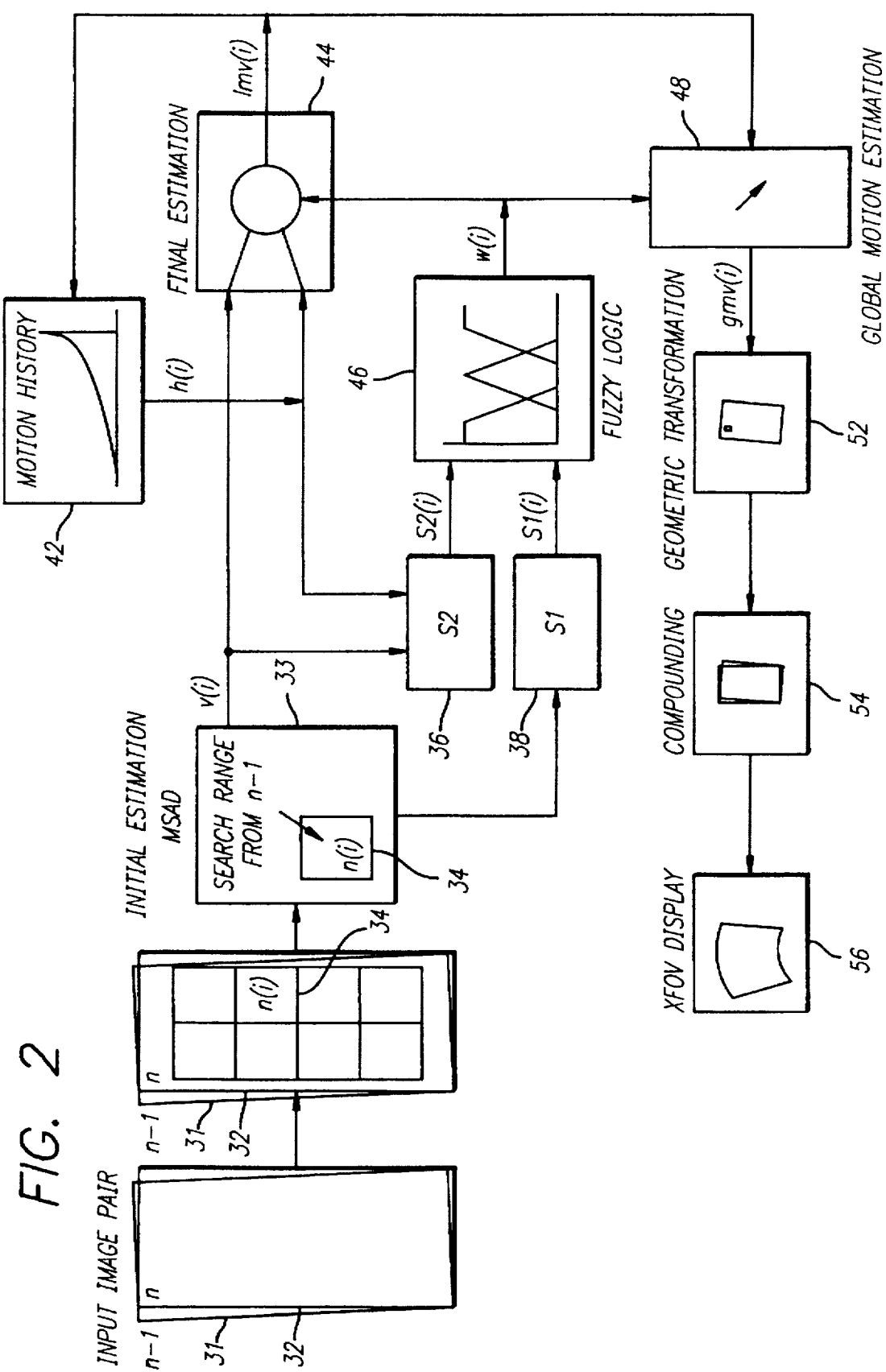
FIG. 2 is a block diagram illustrating an image registration based extended field of view method in accordance with this invention.

FIG. 2 is a block diagram of an image registration based composition method in accordance with this invention. Two consecutive image frames 31, 32 are denoted as frame n-1 (the previous frame) and frame n (the current frame), respectively. The previous image frame n-1 is treated as a reference image. The current image frame n acquired by moving the transducer 16 of FIG. I along the skin surface is compared with the previous image frame n-1 to estimate motion of the transducer. In order to estimate image motion from frame n-1 to frame n, frame n is divided into a plurality of sub-frame regions 34, and the local motion of each of the sub-frame regions is estimated. For I total blocks, the i'th block of frame n is defined as n(i).

The particular size and number of the blocks 34 are selected by consideration of various factors. The block size should approximate the size of the particular image features. For example, image features such as tissue boundaries and blood vessels would require a relatively small block size. Nevertheless, such a small block size would not be suitable for estimation of motion because the small block size decorrelates very rapidly with relatively large magnitudes of motion. Moreover, the small block size would not be stable for in-vivo images where small scale tissue motion exists. At the same time, if the block size is too large, there will be too few blocks per image frame for motion estimation and the motion estimation will be unstable. Further, a large block size may introduce an image rotation error into the local motion estimation where the block is incorrectly assumed to have a translation component but no rotation component.

The block size used in any given implementation of the invention will in general vary with the resolution of the system. The optimum block size in any given case will also depend on the available processing speed and will be determined using both experience and standard experimental techniques. In one working prototype of the invention, a block size of approximately 48×48 pixels was found to be acceptable for motion estimation in view of these factors in relation to an image frame size of about 200×400 pixels. A minimum block size of 32×32 pixels could also be utilized in relation to a smaller image size. In this prototype, these block sizes resulted in a block number between approximately eight and twenty in order to yield the best results.

Figure 3:
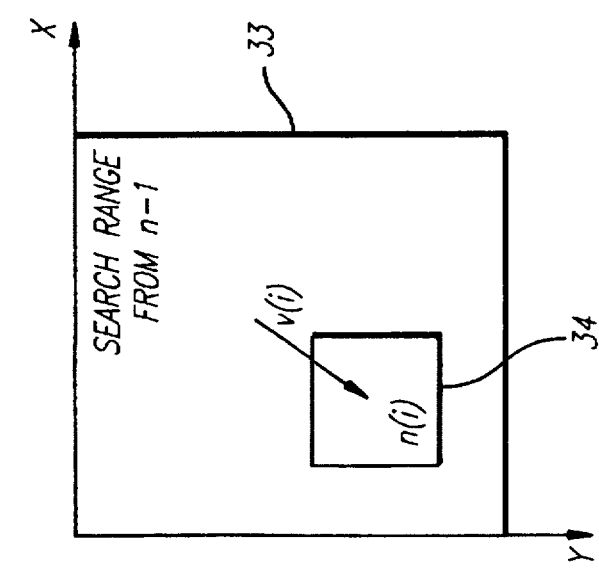
FIG. 3 is a block diagram illustrating a minimum-sum-absolute-difference search of the image registration method.

As illustrated in FIG. 3, local motion of each block n(i) of image n is estimated by moving the block n(i) (such as exemplary block 34) around on the n-1 image frame to find the best match. What is "best," will depend on many factors, including which matching technique one uses in the invention; various alternatives are described below. The search region size 33 on the n-1 image frame is less than the total area of the frame 31, and should relate to the expected image motion speed and image frame rate. For example, a large search region size 33 should be used when the transducer speed is high and also when the image frame rate is low. In the working prototype of the invention, a search region size of 32 pixels in each of the four searching directions was found to be adequate for use with an input image frame rate selected at 7.5 frames/second (computing one out of every four video frames), resulting in a search region size of 64×64 pixels.

In the preferred embodiment of the invention, the "best match" is determined by use of a minimum-sum-absolute-difference technique (MSAD) to match the n(i) block 34 with the search region 33 of frame n-1. Other matching techniques may, however, also be used, and will depend on such factors as the available processing speed and memory capacity. Alternative techniques are discussed below.

Figure 5:
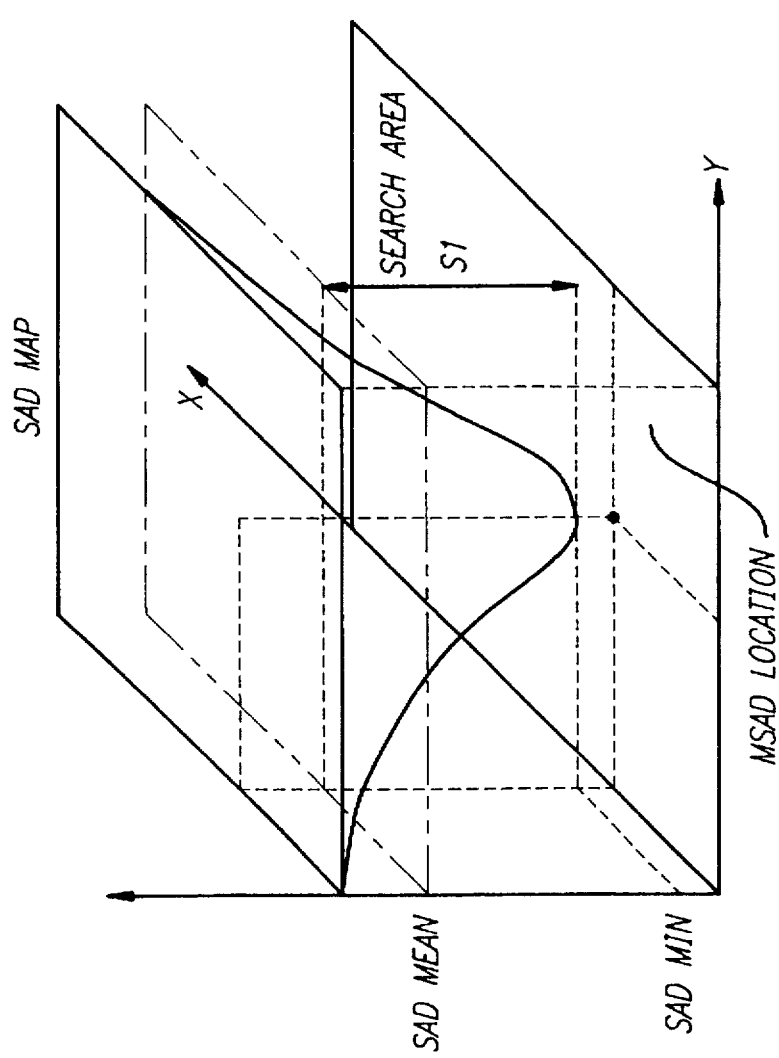
FIG. 5 is a three-dimensional graph illustrating derivation of a quality factor for the minimum-sum-absolute-difference search.

The sum-absolute-difference (SAD) is the sum of absolute differences between corresponding pixel values between each block 34 and the search region 33. The "best match" between the block 34 and the search region 33 occurs where the SAD value is at a minimum. FIG. 5 illustrates a SAD map having values that extend in the X and Y directions. The generally uniform SAD map contains a valley where the SAD values dip below the mean, representing the location of the MSAD. The MSAD technique is used to derive a first estimation of local motion vector v(i) having a direction and magnitude indicating how the block n(i) translated from the n-1 image frame to the n image frame. The direction of the local motion vector v(i) is denoted by the arrow of FIG. 3.

It should be apparent that calculating the MSAD could be a very slow computing process if the number of blocks is large, the block size is large, and the search region is large. For example, a frame n having sixteen blocks 34 with a 48×48 pixel block size and a search region of 64×64 pixels would require about 300,000,000 separate additions/subtractions and about 65,000 comparisons to complete a single MSAD computation. Even with the relatively high speed of conventional processors, this would still encompass too much computation to accommodate real-time application. Accordingly, various search techniques are utilized in order to reduce the magnitude of the MSAD computation.

Figure 4:
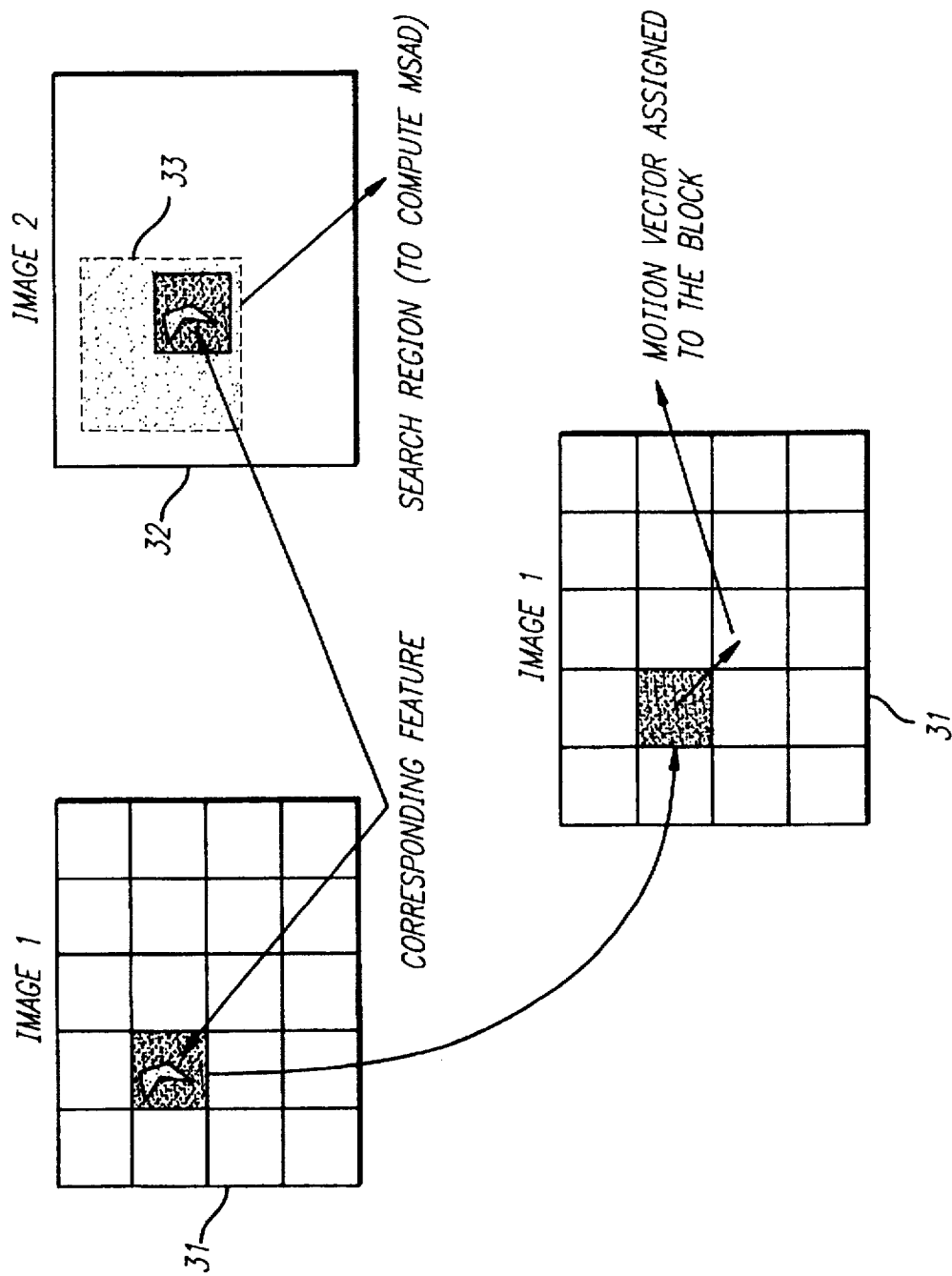
FIG. 4 is a block diagram illustrating an alternative embodiment of the minimum-sum-absolute-difference search.

One such technique for calculating the MSAD utilizes a conventional MPEG encoder. MPEG, or Moving Picture Expert Group, is an industry accepted data compression standard for digitizing graphical information. MPEG encoders are commercially available that can be used to perform a rough estimate of MSAD location based on historical movement of the image. A "best match" is sought between an image characteristic within a block 34 and a search region by searching within a local neighborhood comprising a finite dimensional range, such as within ten pixels in the X and Y directions relative to the image characteristic. In FIG. 4, the location of the MSAD is identified by application of the MPEG encoder, and a local motion vector assigned to the block 34. A drawback of the use of an MPEG encoder is that it results in a high incidence of inaccurate local motion vectors, which must be filtered out.

The accuracy of the local motion vector determination can be further improved by consideration of certain unique constraints of panoramic ultrasonic imaging. Motion in the Y direction (vertical) from one frame to another is almost always smaller than the motion in the X direction (horizontal), because the ultrasonic transducer 16 generally moves only along the patient body contour. This transducer motion can be characterized as being more of a horizontal extension than an up/down folding. Further, the transducer motion is most likely to be in one direction and continuous; sudden reversals in motion direction are not very likely. It has been found from a large number of experiments that MSAD maps are often fairly smooth and continuous even for blocks which have a lot of noise and lack of image features.

In view of these constraints, a fast adaptive coarse/fine MSAD search strategy can be devised that significantly reduces the total amount of computation. The search strategy requires that the search range in the X direction be larger than that in the Y direction, and the search range and direction should be adaptive to the overall motion history. For example, if the history shows the image motion is in +X direction, it is very likely the subsequent frame will also move in the same direction. Because the MSAD map is smooth and continuous, a coarse search can be performed first to reduce the search region 33 to a smaller area, followed by a fine search within the smaller area. Because motion in the Y direction is usually very small (and usually zero), the two-dimensional MSAD search can be reduced to two one-dimensional searches in the X and Y directions, respectively. The first search should be conducted in the X direction to quickly narrow down the search region, followed by subsequent alternating one-dimensional searches in both the X and Y directions to quickly find the MSAD location. Points which have been searched during the coarse search or have been searched in the other direction could be skipped during the fine search.

Based on the above search strategy, in most cases the location of the MSAD can be identified after one coarse and one medium search in the X direction, one coarse search in the Y direction and one small two-dimensional fine search in both directions. For the same example given above, the total number of computations can be reduced to 2,600,000 additions/subtractions and 560 comparisons; representing a reduction of the total number of computations by roughly 115 times.

Under the influence of image noise, tissue motion and other image artifacts, the first MSAD motion estimation is not always very reliable. Accordingly, two measures of the quality and reliability of the first local motion vector estimation v(i) are devised, termed S1(i) and S2(i). As FIG. 5 illustrates, S1(i) is a quality factor of MSAD, and measures the difference between the value of MSAD and mean SAD. MSAD quality increases with the value of S1(i), that is, the deeper the SAD "valley," the better MSAD quality. When strong image noise exists, or when there is a lack of image features, the SAD map will become flatter, so that S1(i) becomes smaller. In that case, the estimation of v(i) becomes less reliable.

One advantage of the MSAD optimization method for determining the best match between two blocks (arrays of pixel values) is that is does not require any multiplications—only additions/subtractions for computation of the SAD similarity of two blocks and then only comparisons in order to find the minimum value on the SAD map. Another advantage is that relatively few memory positions are required for storage of the intermediate values during the calculations. As such, the MSAD method is fast and efficient. On the other hand, the SAD routine may not always be the best at rejecting the influence of certain types of noise, and it does not use any (or much) beforehand knowledge of the known or assumed features of structure, noise or, in the case of ultrasound imaging of the human body, speckle.

Other optimization methods may therefore be used instead depending on the particular imaging environment and on whether the processor used for calculations is fast enough and there is sufficient memory. For example, a least-squares optimization technique may be used, in which the minimum of the sum of the squares of the different pixel pairs in blocks is instead sought and, once found, assumed to be the best match. The least-squares method requires multiplications as well as additions/subtractions, but can be shown to provide a statistically optimal match for certain types of noise.

Even statistically based matching techniques may be used to determine the offset between two image frames. For example, the correlation between speckle found in two frames of ultrasonic imaging data can be shown, under certain known conditions, to be related to the distance between the two frames. Such statistical techniques may also be used in the invention to provide a measure of the "best" match between frames or blocks.

Refer now to FIG. 6. The second parameter S2(i) measures how much v(i) deviates from its past history. The motion history 42 of the i'th block, h(i) (also shown in FIG. 2), is the recursively weighted averaging of previous final local motion vector outputs of the i'th block. S2(i) is the vector difference between v(i) and h(i). Generally, image motion is fairly smooth and consistent for both experienced and un-experienced ultrasound operators. If one value of v(i) has a very different direction and magnitude as compared with its history, it is very likely that this estimation is under the influence of noise or local tissue motion and does not accurately reflect true image local motion. In this case the v(i) estimation is not very reliable. Thus, a large value of S2(i) indicates that the estimated v(i) is less reliable.

While the above estimation quality control concept is easy to understand, in practice it is difficult to implement since image changes caused by transducer motion can be rather complex. Accordingly, the quality and reliability of the motion estimate can be efficiently quantized by use of fuzzy logic, which is included in the preferred embodiment of the invention. As FIG. 2 shows, a fuzzy logic control block 46 receives S1(i) and S2(i) as inputs, combines them using fuzzy rules (described below), and produces a single numerical output w(i) which represents a degree of accuracy of v(i). The numerical output w(i) ranges from zero to one, with the estimation accuracy of v(i) increasing as w(i) approaches one.

Figure 7A:
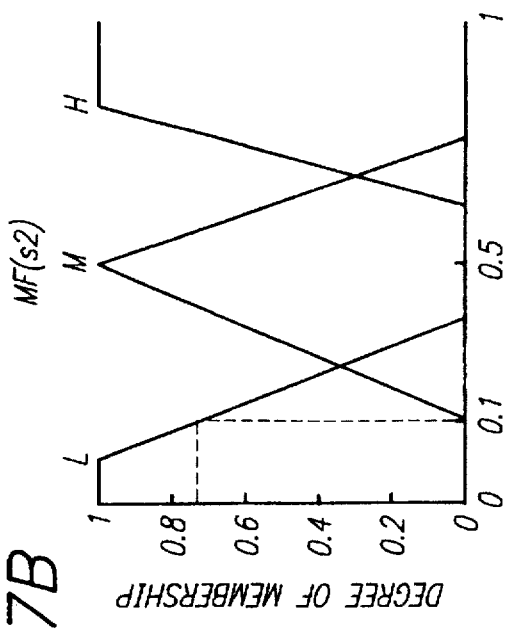
FIGS. 7A through 7D are graphs illustrating fuzzy logic membership functions for the quality factor and the deviation factor to derive a control value and a single numerical output.
Figure 7B:
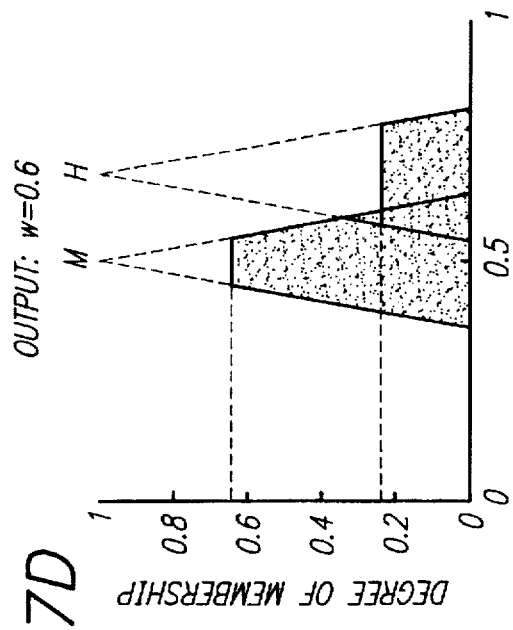
Figure 7C:
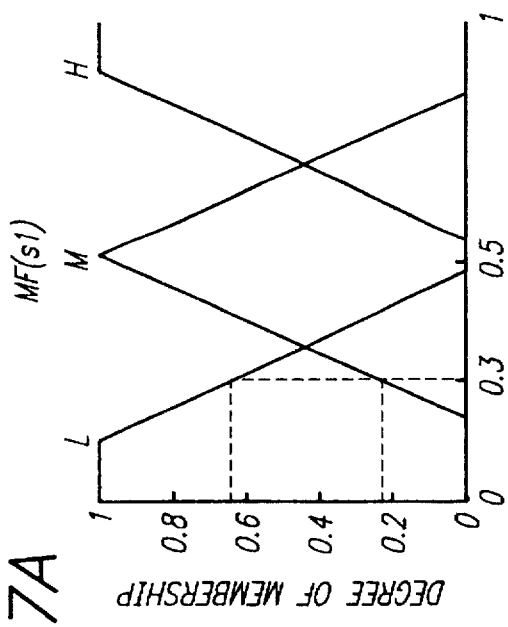

The inputs S1(i) and S2(i) are first "fuzzified" into the linguistic expressions, or labels, "high", "medium" and "low". Output w(i) also has its fuzzy expression as "very high", "high", "medium", "low" and "very low". Membership functions of S1(i), S2(i) and w(i) are defined from a large number of experimental results, and are illustrated in FIGS. 7A through 7C, respectively. The membership function of S1(i) is graphically illustrated at FIG. 7A as comprising three regions labeled as L (low), M (medium) and H (high). The regions overlap to a certain extent; specifically, the L and M regions overlap, and the M and H regions overlap. The horizontal axis of the membership function graph defines the measured value of S1(i), and the vertical axis defines the degree of membership of the measured value within the defined label.

The membership function of S2(i) is graphically illustrated in FIG. 7B, and is constructed similar to the membership function of S1(i). Similarly, the membership function of w(i) is graphically illustrated in FIG. 7C, and is constructed similar to the membership functions of S1(i) and S2(i), though it includes five overlapping regions labeled as VL (very low), L (low), M (medium), H (high), and VH (very high).

Seven fuzzy rules are used to define the relationship between S1(i), S2(i) and w(i). These fuzzy rules include:

(1) If S1(i) is low (L) AND S2(i) is also low (L), then w(i) is medium (M);

(2) If S1(i) is medium (M) AND S2(i) is low (L), then w(i) is high (H);

(3) If S1(i) is high (H) AND S2(i) is low (L), then w(i) is very high (VH);

(4) If S1(i) is low (L) AND S2(i) is medium (M), the w(i) is low (L);

(5) If S1(i) is medium (M) AND S2(i) is also medium (M), then w(i) is medium (M);

(6) If S1(i) is high (H) AND S2(i) is medium (M), then w(i) is high (H); and (7) If S2(i) is high (H), then w(i) is very low (VL).

Other fuzzy rules and membership functions may be used instead of those given above and can be determined using normal experimentation. The rules and function above, however, gave satisfactory results in prototypes of the invention. The fuzzy rules are applied in parallel to determine the truth of the rules. For example, assume that measured values of S1(i) and S2(i) are 0.3 and 0.1, respectively. In FIG. 7A, a measured value of 0.3 relates to degrees of membership of approximately 0.65 in the L label and approximately 0.25 in the M label. In FIG. 7B, a measured value of 0.1 relates to a degree of membership of approximately 0.75 in the L label only. As a result, only the first two fuzzy rules are true, though they yield inconsistent results in that the first fuzzy rule concludes w(i) is medium and the second fuzzy rule concludes that w(i) is high. The output w(i) must be converted back to a numerical value, and the inconsistent results must be reconciled.

Figure 7D:
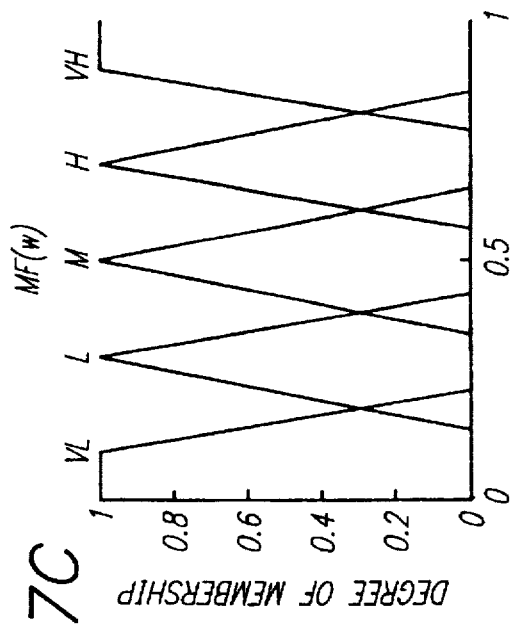

Under the first fuzzy rule, the low value of S1(i) is combined using a logical AND with the low value of S2(i) to provide the medium value of w(i). Under the logical AND operation, the minimum value of the truth of the expressions is taken as the truth level of the rule. In other words, the 0.65 degree of membership of S1(i) is less than the 0.75 degree of membership of S2(i), and is thus taken as the truth level for the first fuzzy rule. Similarly, under the second fuzzy rule, the medium value of S1(i) is combined using a logical AND with the low value of S2(i) to provide the high value of w(i). The 0.25 degree of membership of S1(i) is less than the 0.75 degree of membership of S2 (i), and is thus taken as the truth level for the second fuzzy rule. The M and H labels of the w(i) membership function are then truncated at the truth levels defined by the fuzzy rules, as illustrated graphically in FIG. 7D.

Finally, a centroid defuzzification technique is used to convert the fuzzy output back to a numerical number w(i). Using this technique, an estimate of the center of gravity is provided for the entire region determined to be true (illustrated as the shaded region of FIG. 7D). From FIG. 7D, the center of gravity of the shaded region is approximately 0.6, providing a numerical value for w(i).

After the reliability parameter w(i) is obtained, the next step is to use w(i) to improve the local motion estimation v(i). If w(i) is large, v(i) is used directly as the final local motion vector lmv(i). In contrast, if w(i) is very small, the average frame motion history h(i) is used as the estimated lmv(i), since the motion history is more likely to be a better estimation than the less reliable v(i). If w(i) is neither very large nor very small, it is used as a weighing factor to average v(i) and h(i). For instance, if w(i)=0.6, as in the above example, then lmv(i)=0.6*v(i)+(1−0.6)*h(i).

The motion history h(i) is also updated recursively by weighting lmv(i). The weight is selected to be between zero and one; a larger weight value makes the very recent motion estimation contribute more to the history h(i). For example, if the weight is 0.5, then h(i) is set equal to 0.5*lmv(i)+(1−0.5)*h(i).

Once all of the local motion vector outputs lmv(i) are estimated for the n'th frame, the outputs are combined together at 48 of FIG. 2 to estimate the frame global motion vector, gmv(i). Minimum least-squares (L-S) error parameter fitting is preferably used to combine the motion vector outputs, using three optimization parameters including frame translation (Xn, Yn) and rotation ⊖n. The weighted L-S gives the local motion vector v(i) which has a larger w(i) more weight than those having smaller w(i). This way, the more reliable local motion vectors v(i) contribute more heavily to the optimization process.

The geometrically corrected frames are combined together at 54 of FIG. 2 to form a panoramic image. Three examples of techniques that can be applied to combine the corrected frames are: "image growing," which only puts new pixel data in the non-overlapping part to the panoramic image buffer; "recursive spatial compounding," which recursively averages the new image frame with existing panoramic image; and "ramp compounding," which gives weight ramps for both the new image frame and the existing panoramic image in the overlapping area. This latter technique successfully reduces panoramic image local discontinuity caused by motion jitters. Finally, the panoramic image is displayed on a video display terminal 56 or other such device, providing the full image represented in phantom on the terminal 22 of FIG. 1, described above.

It should be apparent that the above method and apparatus for generating a panoramic image is applicable to both real-time imaging and re-generation of recorded image information. In application, a physician may use a conventional ultrasonic imaging system to produce image frames that are recorded onto a permanent storage medium, such as tape. Subsequently, the image frames could be processed into a panoramic image for later viewing by the physician by bringing the recorded image frame data to a viewing station. The viewing station would then process the image frame data by use of the method described above to generate a panoramic image. It should also be apparent that the method and apparatus of this application are not limited to processing of ultrasonic images, but would be equally applicable to other imaging modalities, such as radar or photographic imaging.

Figure 8:
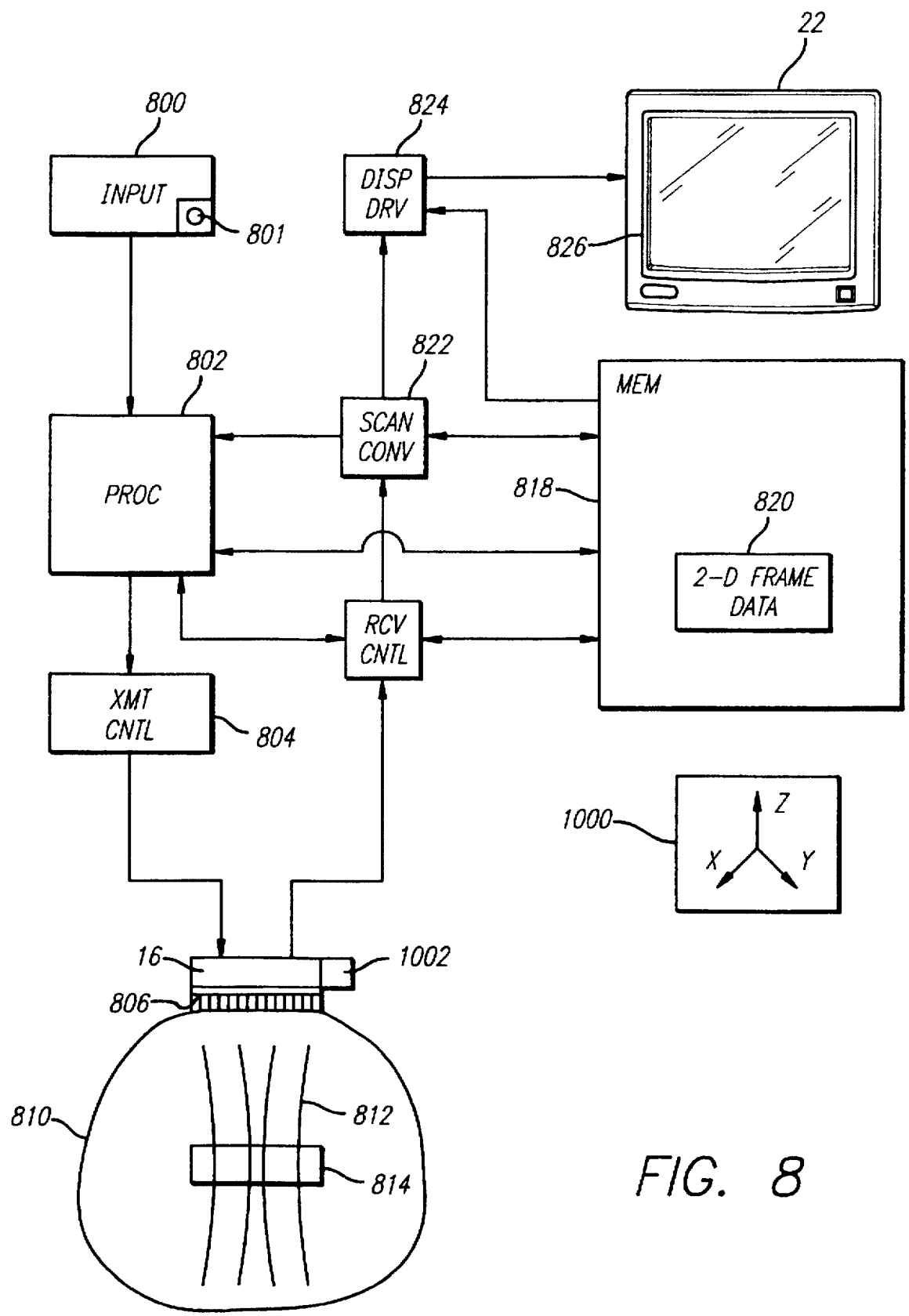
FIG. 8 is a block diagram of an ultrasound system according to the invention.

FIG. 8 illustrates the main components of an ultrasonic imaging system according to the invention. The user enters various conventional scan parameters into an input unit 800, which typically includes such devices as a keyboard, knobs, and buttons, and a cursor-control device such as a trackball 801 or mouse. The input unit is connected to a processing system 802, which will typically be an electrically connected and cooperating group of processors such as microprocessors and digital signal processors; the processing system may, however, also be implemented by a single processor as long as it is fast enough to handle the various tasks described below. The processing system 802 preferably includes the image processor 20 shown in FIG. 1.

As in known systems, the processing system 802 sets, adjusts, and monitors the operating parameters of a conventional transmission control circuit 804, which generates and applies electrical control and driving signals to the ultrasonic probe 16 (see also FIG. 1) which includes an array 806 of piezoelectric elements. As is well known in the art, the piezoelectric elements generate ultrasonic waves when electrical signals of the proper frequency are applied to them.

By placing the probe 16 against the body of a patient, these ultrasonic waves enter a portion 810 of the patient's body. By varying the phasing, amplitude, and timing of the driving signals, the ultrasonic waves are focussed to form a series of scan lines 812 that typically fan out from the probe. Several such scan lines are shown extending into the patient's body in FIG. 8. A region of interest, that is, the region that the user wants to have an image of, is shown as an interrogation region or volume 814. The manner in which ultrasonic scanning signals are controlled, generated, and applied to a patient's body is well understood in the art and is therefore not described further.

Ultrasonic echoes from the waves transmitted into the body return to the array in the probe 16. As is well understood, the piezoelectric elements in the array thereby convert the small mechanical vibrations caused by the echoes into corresponding electrical signals. Amplification and other conventional signal conditioning is then applied to the return signals by a reception controller 816. This processing includes, as needed, such known signal conditioning as time-gating, gain compensation, and diffraction compensation, in order to identify the echo signals that correspond to each scan plane of the interrogation volume 814.

The reception controller 816, all or part of which may be integrated into the processing system 802 itself, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging. The down-converted power values for the two-dimensional interrogation region are stored in a memory 818 as 2-D frame data 820, after conventional beamforming. Each set of frame data corresponds to one image frame, that is, to a 2-D cross section of the interrogation volume. Each frame of the image is represented and stored digitally as an array of acoustic power or intensity values for the image elements that make up the frame.

The interrogation region is normally not in the same shape as what the user wants to see displayed, and even when it is, the digital acoustic intensity values formed into beams are normally not in a form suitable for driving a conventional gray-tone or color display directly. The acoustic intensity values for an image frame are therefore applied to a conventional scan converter 822, which converts the digital acoustic values into display intensity or brightness values that are suitable for use in driving the display device 22 (see also FIG. 1). The display device 22 typically includes or is connected to a display driver 824 and a screen 826 (for example, LED or CRT) that is divided into an X-Y (or polar) matrix or pattern of picture elements or "pixels" that make up an image that the user can view and interpret.

The image is displayed as a pattern of image elements that correspond to the received intensities from corresponding portions of one 2-D frame of data from the interrogation region. Note that a displayed image element will often be made up of more than one pixel, but that this will depend on the relative resolutions of the scan and of the display. The invention does not require any particular relative resolution.

Ultrasonic imaging may be done in any of several modes. Two common modes are the power or power-Doppler mode and the color mode. In the power-Doppler mode, the display is typically gray-tone, and the displayed intensity of each pixel corresponds to the amplitude of the power of the return signal from a corresponding element or portion of the interrogation region. In other words, the stronger the acoustic echo is (in amplitude, degree of Doppler shift, or some other conventional signal characteristic) from a portion of the scanned region, the more brightly it is displayed. Note that it is also possible to display intensity data using "pseudo-colors," that is, such that different intensities (or intensity intervals) are displayed using different assigned colors. For example, increasing intensity can be displayed as increasingly more red.

Figure 9:
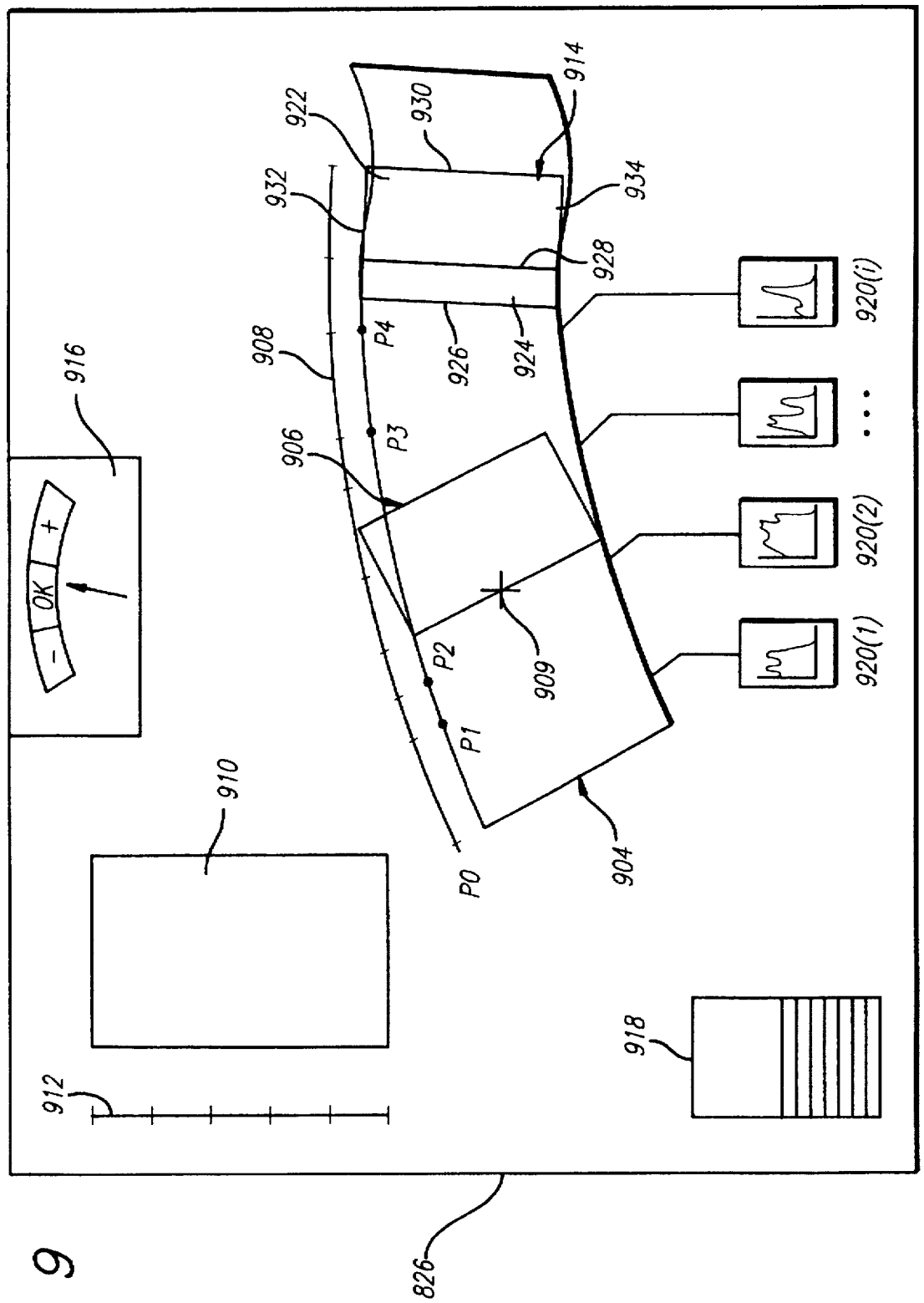
FIG. 9 illustrates a display that the system according to the invention generates, including several auxiliary but optional display features.

FIG. 9 illustrates one example of a panoramic image display 826 that the invention can generate. In addition to a panoramic image 904, the illustrated display show the following inventive features, any, all or none of which may be included in the display:

a flexible ruler 908;

a zoom frame indicator 906;

a zoom frame display 910 with a depth scale 912;

a guide frame 914;

a transducer speed indicator 916;

a memory availability map 918; and a plurality of spectral icons 920(1), 920(2), . . ., 920(i).

These features are described individually below.

As FIG. 9 illustrates, the panoramic image displayed by the invention will in many—indeed, most—cases be "curved", that is, it will represent a view of the interrogation region resulting from non-linear motion of the transducer. As such, the individual image frames, such as the substantially rectangular frame 906, will be "bent," since only a portion of the frame is registered and compounded with the previous frame(s), which will often have a slightly different orientation.

The processing system 802, however (especially the image processor 22), shown in FIGS. 8 and 1, respectively, determines the distance between pixels in a frame (or in different frames) as part of conventional beamforming and scan conversion processing, or as a result of estimating local and global motion using this invention. Consequently, the physical distance within the interrogation region between any two displayed pixels is also determined. As such, the processing system, by examining frame data in memory or by a process of accumulation of incremental distance calculations, can determine which of two displayed pixels are a given linear, physical distance apart or, conversely, what linear separation two given displayed pixels represent. For example, the processing system will already have generated data that would indicate that pixels P1 and P2 represent the same physical separation as the pixels P3 and P4.

In the preferred embodiment of the invention, the processing system 802 therefore determines where, along some edge or intermediate measurement line, pixels lie at multiples of a predetermined incremental physical distance away from a from predetermined end point P0. A line 908 is then preferably generated (via the display driver) and displayed adjacent to the measured edge or line, with tick marks or other indicators at the various multiples of the incremental distances. By viewing this "flexible ruler," the user will thus be able to see that the physical distance represented between pixels P1 and P2 is the same (one tick mark) as the distance represented between pixels P3 and P4. The tick marks or other indicators may be in any predetermined unit of length, or they may be generated by the processing system to represent predetermined fractions of the overall length of the panoramic image. The line 908 is preferably piecewise linear, since this will give the user the best feel for the linear distance between the represented points. Other approximating functions such as splines may, however, also be used to generate the line 908.

Using known techniques, the processing system 802, via the display driver 824, is able to sense the operation of the trackball, mouse or other pointer 801 and generate a cursor 909 on the display screen and relate the cursor position to the position of individual pixels in the panoramic display 904. Note further that the position of any given pixel will also correspond to the leading or trailing edge of one stored data frame, such as frame 906. In the preferred embodiment of the invention, the user may maneuver the pointer 801 to select a frame of particular interest, which the processing system then recalls from either the frame data memory 820 and displays in its uncompounded form as a zoom frame 910, which is preferably displayed with the panoramic image.

Note that the zoom frame will be generated in undistorted form, that is, in the form before compounding with other frames. The relative distances between pixel pairs in the zoom frame are thus as they are sensed during scanning. A depth scale 912 is therefore preferably also generated and displayed beside the zoom frame 910, with tick marks (for example) indicating predetermined units of length.

As an alternative to the cursor-directed frame-selection procedure described above, the user may instead maneuver the input device 801 to recall frames sequentially from a cine memory, with the processing system 802 then displaying the outline of each respective frame as a superimposed rectangle 906 (or other corresponding shape) on the panoramic image display 904. The zoom frame 910 may then still be displayed as described above.

During generation of the panoramic image 904, only a portion of each currently generated frame is actually compounded with previous frames. In FIG. 9, a frame 914 is shown as having a compounding portion 924 between lines 926 and 928; the non-compounded portion 922 of the frame between lines 928 and 930 represents a valid portion of the frame data, and is stored in the frame memory 820. The non-compounded frame portion 922 indicates, moreover, what "lies ahead" of the transducer, that is, it indicates what image features lie in the region which would fall in a compounding portion of a subsequent frame if the user were to move the transducer perpendicular to the line 928.

In the preferred embodiment of the invention, the processing system, via the display driver, displays the outline of the current frame 914, as well as the line dividing the compounding from the non-compounding portion of the frame. In other words, the system displays the line segments 926, 928, 930, 932 and 934. As the user moves the transducer, he will thus be able to see what lies ahead of the current frame and can thus better see how he should move the transducer to include in the panoramic image those features of greatest interest to him.

As is mentioned above, if the user moves the transducer too fast, then the system may not be able to generate and correlate frames fast and accurately enough to create a reliable compound image. Moreover, if the user moves the transducer too slowly, then the system's memory may fill with frame data that is duplicative, or not needed in order to produce a composite image of acceptable reliability and scope. The processing system therefore computes the momentary speed with which the user is moving the transducer from the values for local and global vector motion, since the time base is known.

In the preferred embodiment of the invention, a "speedometer" display 916 is generated, which indicates to the user whether he is at any given moment moving the transducer within acceptable speed limits. In the example illustrated in FIG. 9, the display is in the form of a meter with three fields: too slow (−), acceptable (OK), and too fast (+), with a displayed needle indicating the current speed by its orientation. In FIG. 9, the user is moving the transducer a bit fast, but still within the acceptable speed range. Other indicators may, however also be displayed, for example, a "speed" display field could be shown in different colors (for example, blue, yellow, red) to indicate the various speed ranges.

It is also helpful to the user to know roughly how many more image frames can be stored, compounded, and thus included in the panoramic image. In the preferred embodiment of the invention, the processing system therefore monitors the available capacity of the frame data memory 820 and generates a memory map icon 918 or bar on the display to indicate this. As the frame data memory fills, more and more of the icon is filled by different coloring. In the example illustrated in FIG. 9, the image memory is about half full. Other indication icons may also be used, for example, those with a numerical indication of memory availability.

It is known to generate spectral Doppler data for ultrasonically generated data frames, along with the intensity data. In one embodiment of the invention, spectra are computed in the conventional manner for each of a predetermined number of data frames that go into making up the panoramic image. Lead lines leading to the respective frames (regions of the panoramic image 904 where the frames were used in compounding) may then be displayed leading from respective 920(1), 920(2), . . ., 920(i) image icons that graphically represent the spectra.

As is mentioned above, many ultrasonic image systems are able to generate images not only as functions of the echo intensity from different parts of the interrogation region, but rather they may work in other velocity or speed-based modes, and they represent the speed or velocity using color coding. These include "power mode," in which the displayed color for any given pixel is a function of the speed of movement in the corresponding physical region; "Doppler mode," in which the color is a function of the velocity (direction-dependent) in the corresponding sample volume; and "color mode," in which a color-coded velocity map is displayed.

As one color-coded embodiment of the invention, the colors for each pixel in the panoramic image are also computed in the conventional manner and are then displayed as such. In other words, the panoramic image itself is color-coded with the power or Doppler information. In order to ensure that the various compounded image frames are color-coded in a comparable way to yield consistent information, frame generation may be triggered by some related, recurring event. For example, for color-coded panoramic imaging of the flow of blood in the heart, the processing system 802 may receive signals from an EKG machine so as to trigger each frame at the same point in the heart cycle; the cycles of the heart may also be tracked from the image data themselves, so that no external device would be necessary for triggering.

Refer once again to FIG. 8. Although the preferred embodiment of the invention is able to generate panoramic images without any hardware sensors attached to the transducer probe, external motion sensing may be incorporated into the invention, for example, for the purpose of calibrating the system, or to reduce the computational burden (for example, in the MSAD routine) by directly estimating at least the coarse motion of the probe. A motion sensor 1002 may therefore be attached to the probe 16 and, depending on the chosen sensor, an external reference source 1000 may be included. If the motion sensor is, for example, a set of accelerometers, then no external source 1000 will be necessary. If a Polhemus sensor is used, however, then the external source will generate the set of orthogonal magnetic waves used by the transducer-mounted sensor.

At present, there are no commercially available phantoms that are suitable for testing and calibration of a panoramic image-generating system such as the invention. The invention works on image structures, such as blood vessels, organ boundaries and so on. Many available phantoms are not long enough to provide a suitable test region for generating a panoramic image. Most available phantoms, moreover, have only a few wire targets in a flat, structure-free background, and image contents from such phantoms are much less than from real tissue.

According to the invention, an ultrasound phantom contains embedded contrast structures. In one prototype, large-hole sponges were mounted on precisely located wires within the phantom. In another prototype, in addition to conventional wires to simulate point targets, substantially spherical targets of roughly 10mm diameter ±10% with a contrast from +15dB to −15dB relative to the background were included in the phantom housing. Other shapes may, of course also be used, although they will in general have less well understood reflection characteristics. Attenuation of the spheres and the background was roughly 0.5dB/cmMhz ±0.05 dB/cmMHz. In one prototype, fine glass beads served adequately as scatterers for the spherical targets, which were made from the same material as the background filler so as to have the same speed of sound and attenuation.

FIG. 10a is a side view of one prototype test phantom according to the invention. Above a top surface 100 of the phantom are preferably a transparent, permanently attached lip 102 to hold water and a hinged, removable lid 104 to slow desiccation. A handle 106 is also shown. In the illustrated prototype, 72 targets were included, which are shown as dots having the various spacings indicated in the figure.

FIG. 10b is a top view of the test phantom shown in FIG. 10a. As FIG. 10b shows, the top of the phantom prototype presented an acoustic window 108 with the indicated dimensions.

Figure 10C:
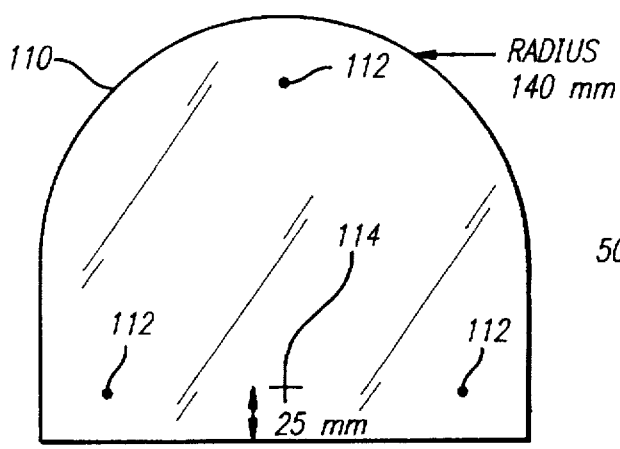
FIGS. 10$a$–10$g$, 11$a$–11$c$, and 12 show different embodiments and structural features of test phantoms suitable for calibrating and testing the panoramic image-generation system according to the invention.

FIG. 10c illustrates a transparent, removable guide plate 110 that bolts onto the side of the phantom (see FIG. 10a). In the illustrated prototype, alignment pins 112 extended through the guide plate so as to fit either snugly against the outside of the phantom, or into indentations in the side of the phantom, whichever is more convenient in a given application. A through-hole 114 was also included for a bolt to hold the plate onto a matching threaded hole in the phantom itself.

Figure 10D:
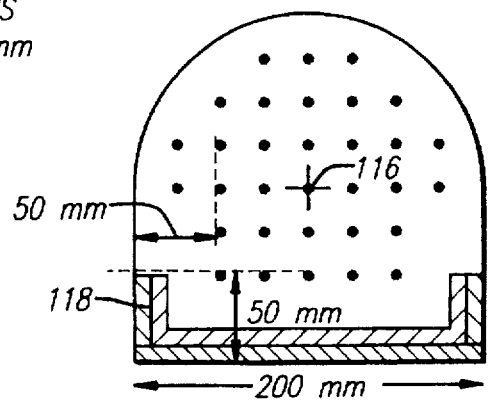

FIG. 10d is a side view of the prototype test phantom according to the invention with 32 line targets distributed on a 5-by-5 grid with 25 mm separation, plus seven outlying targets. A cross hair mark 116 was included on the outside of the phantom, at its center and an acoustic absorber 118 was installed as a liner for the sides and bottom of the phantom.

Figure 10E:
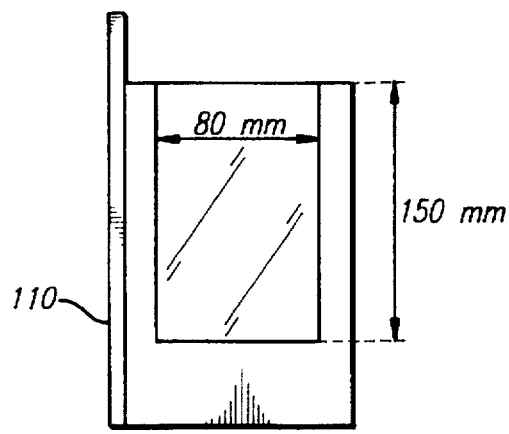
Figure 10F:
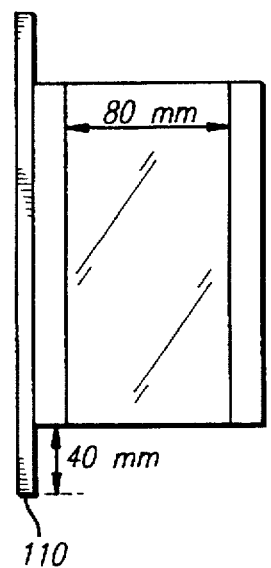

FIGS. 10e and 10f are end and top views, respectively, that show the dimensions of the acoustic window presented by the phantom, as well as the position of the removable guide plate 110.

Figure 10G:
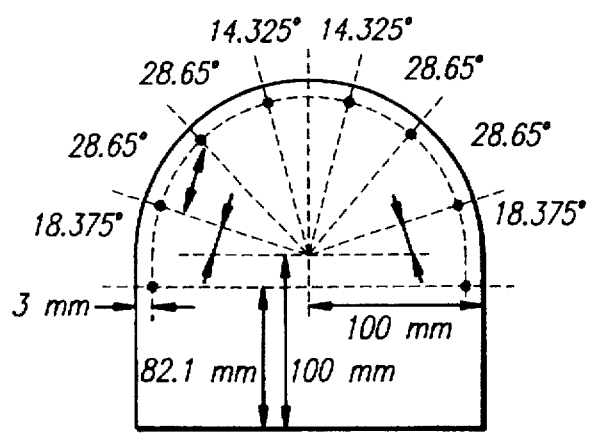

FIG. 10g illustrates the positions of eight additional line targets arrayed in the phantom along an arc near its edge. These targets were included along with the grid of targets shown in FIG. 10d but are shown here separately to more clearly show the different distribution pattern of these line targets.

Figure 11C:
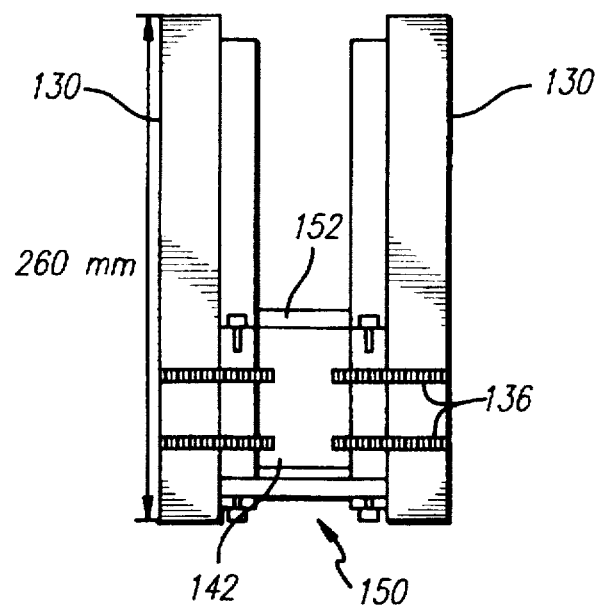

FIG. 11a is a side view of a prototype of an embodiment of the test phantom according to the invention that included a total of 92 target wires (line targets). As FIG. 11a shows, this embodiment includes a reinforcing aluminum frame 130 that is bolted using bolts 136 to the sides of the phantom via legs 132 that are strongly bolted and bonded to the phantom. Dowel holes 134 were provided through the legs 132 for accurate alignment of the two sides of the phantom and frame using an alignment dowel 150 (FIG. 11c).

FIG. 11b is a top view of the reinforcing frame 130 shown in FIG. 11a. As this figure illustrates, the frame 130 in the illustrated prototype consists of two parallel, substantially identical members. The bolts 136 pass through the legs 132 and the side walls 138 of the phantom and are screwed into mating threads 140 in an end wall 142 of the phantom.

For each wire target, a pair of opposing holes 144, 146 is made in respective sides of the phantom. In the prototype, the holes were of different sizes, with one 144 hole having an outer diameter of about 7.9375 mm (5/16 inch) and an other hole having an outer diameter of about 9.525 mm (3/8 inch). The inner holes through which the wires entered into the interior of the phantom were about 0.6096 (0.024 inch) in diameter.

FIG. 11c is and end view of the frame/leg structure shown in FIGS. 11a and 11b. The alignment dowel 150 spaces the two halves of the frame and the end wall 142 of the phantom has a beveled top 152.

Figure 12:
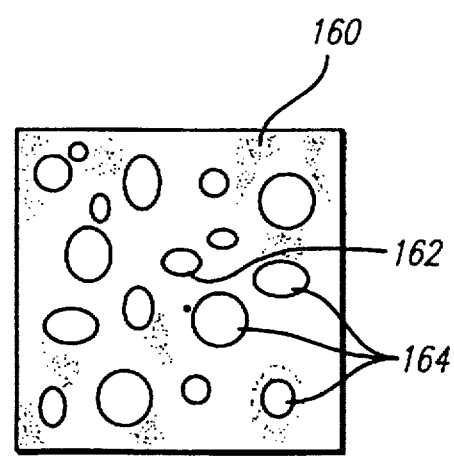

FIG. 12 illustrates an example of the material used to fill the phantom according to the invention. As in conventional phantoms, the phantom according to the invention is mostly filled with a background material 160. Wire line targets 162 preferably extend through the phantom with the distributions shown, for example, in FIGS. 10a, 10d, 10g and 11a.

In addition to the wire targets, however, the phantom according to the invention includes random scattering structures 164 that provide more realistic and more easily visualized and interpreted returns useful for building up and testing a panoramic image such as is generated by the system according to the invention. The random scatters may, for example, comprise any of the scatterers mentioned above, such as the large-hole sponges mounted on the target wires, the substantially spherical targets (for example, glass beads), or variable-shaped reflectors such as those illustrated.

FIGS. 10a–10g, 11a–11c, and 12 show and describe different embodiments and structural features of test phantoms suitable for calibrating and testing the panoramic image-generation system according to the invention.

What we claim is:

1. A method for generating a compound image comprising the steps of:

generating a plurality of substantially adjacent image frames of an interrogation region of a patient's body, in which the adjacent frames may be at least partially overlapping;

dividing individual ones of the image frames into a plurality of sub-image regions;

estimating local motion vectors of the respective sub-image regions between consecutive ones of the image frames;

estimating global image motion based on the estimated local motion vectors;

generating and displaying a compound image based on the estimated global image motion; and generating and displaying real-time probe guide information in addition to the compound image as the compound image itself is being generated and displayed.

2. A system for generating a compound image comprising:

means for generating a plurality of substantially adjacent image frames of an interrogation region of a patient's body in which the adjacent frames may be at least partially overlapping;

means for dividing individual ones of the image frames into a plurality of sub-image regions;

means for estimating local motion vectors of the respective sub-image regions between consecutive ones of the image frames;

means for estimating global image motion based on the estimated local motion vectors;

means for generating and displaying a compound image based on the estimated global image motion; and means for generating and displaying real-time probe guide information in addition to the compound image as the compound image itself is being generated and displayed.

3. The method defined in claim 1, the step of generating and displaying real-time probe guide information including the following sub-steps:

estimating the physical distance in the interrogation region between selected points displayed in the displayed compound image;

generating and displaying a distance scale corresponding to the estimated physical distance between the selected points adjacent to and following a contour of the displayed compound image.

4. The method defined in claim 1, further including the step of simultaneously displaying, along with the compound image, at least one of the image frames as an undistorted, secondary displayed image.

5. The method defined in claim 4, further including the following steps:

sensing user selection of a portion of the compound image;

displaying as the undistorted, secondary frame the image frame corresponding to the user-selected portion.

6. The method defined in claim 4, further including the following steps:

calculating an depth scale corresponding to depths of portions of the undistorted, secondary frame within the interrogation region; and displaying the depth scale adjacent to the undistorted, secondary frame.

7. The method defined in claim 1, in which the plurality of substantially adjacent image frames of the interrogation region is generated by a transducer being moved by a user over the surface of the patient's body, the step of generating and displaying real-time probe guide information including the following sub-steps:

estimating a speed with which the transducer is being moved over the patient's body while the compound image is being generated and displayed;

calculating a maximum transducer speed limit corresponding to a maximum image frame compounding rate; and displaying an indication of the maximum transducer speed limit, along with a marking indicating the estimated speed of motion of the transducer relative to the maximum transducer speed limit.

8. The method defined in claim 7, in which the step of generating and displaying real-time probe guide information further includes the following sub-steps:

calculating a minimum memory-efficient transducer speed limit as a predetermined function of a maximum image frame memory storage capacity; and displaying an indication of the minimum transducer speed limit, along with the marking indicating the estimated speed of motion of the transducer relative to the maximum transducer speed limit.

9. The method defined in claim 1, in which the image frames are stored as image frame data in an image frame memory, and in which the step of generating and displaying real-time probe guide information further includes the following sub-steps:

while generating and displaying the compound image, determining a measure of remaining memory availability corresponding to an amount of the image frame memory not yet containing image frame data relative to a total image frame memory capacity; and;

displaying an indication of the measure of the remaining memory availability.

10. The method defined in claim 1, in which:

the step of generating and displaying the compound image comprises:

dividing a current image frame into a compounding and a non-compounding portion;

for each currently generated image frame, compounding only its compounding portion into the previously compounded image; and the step of generating and displaying real-time probe guide information further includes the following sub-steps:

displaying the non-compounding portion of the current image frame as an undistorted look-ahead extension of the compounded image; and marking the displayed look-ahead extension.

11. The method defined in claim 1, further including the step of superimposing color-coded image power information on the displayed compound image.

12. The method defined in claim 1, further including the step of superimposing color-coded Doppler image information on the displayed compound image.

13. The method defined in claim 1, further including the following steps:

computing a Doppler spectrum for each of a predetermined plurality of image frames included in the compound image; and displaying a representation of each computed Doppler spectrum adjacent to the portion of the displayed compound image corresponding to each respective corresponding image frame.

* * * * *